(12) United States Patent
Kuhnicke et al.

(10) Patent No.: US 6,276,208 B1
(45) Date of Patent: Aug. 21, 2001

(54) COMPONENTS MADE OF DUCTILE METALLIC MATERIAL AND METHOD FOR DETERMINING DEFORMATIONS AND/OR STRAINS BY MEANS OF SOUND EMISSION ANALYSIS

(75) Inventors: Horst Kuhnicke, Dresden; Lothar Schneider, Coswig; Gustav Zouhar; Ulf Waag, both of Dresden, all of (DE)

(73) Assignee: Fraunhofer-Gesellschaft zur Forderung der Angewandten Forschungen E.V., Munich (DE)

( * ) Notice: Subject to any disclaimer, the term of this patent is extended or adjusted under 35 U.S.C. 154(b) by 0 days.

(21) Appl. No.: 09/341,942
(22) PCT Filed: Jan. 19, 1998
(86) PCT No.: PCT/DE98/00162
§ 371 Date: Aug. 31, 1999
§ 102(e) Date: Aug. 31, 1999
(87) PCT Pub. No.: WO98/31490
PCT Pub. Date: Jul. 23, 1998

(30) Foreign Application Priority Data

Jan. 20, 1997 (DE) .............................. 197 01 776

(51) Int. Cl.⁷ .............................. G01D 7/00; G01N 29/04
(52) U.S. Cl. .............................................. 73/587; 73/801
(58) Field of Search .............................. 73/579, 587, 801, 73/1.83

(56) References Cited

U.S. PATENT DOCUMENTS

| | | | |
|---|---|---|---|
| 4,297,885 | * 11/1981 | Hein, Jr. et al. | 73/587 |
| 4,704,892 | * 11/1987 | Tarnai | 73/1.86 |
| 4,944,185 | * 7/1990 | Clark, Jr. et al. | 73/579 |
| 5,024,092 | * 6/1991 | Harrold et al. | 73/602 |
| 5,814,734 | * 9/1998 | Chang et al. | 73/819 |

OTHER PUBLICATIONS

Jayakumar et al., "Influence of MC–Type Carbides on Accoustic Emission Generated during Tensile Deformation in a Nimonic Alloy," J. Acoustic Emission, V. 11(1), pgs 43–51 (1993).

* cited by examiner

Primary Examiner—Max Noori
(74) Attorney, Agent, or Firm—Barnes & Thornburg

(57) ABSTRACT

The invention relates to components made from ductile metallic materials, and to a method with which deformation or the load acting on these materials is to be determined by means of acoustic emissions analysis. For this purpose, a particulate substance which is brittle at least in the temperature range below 400° C. is added to the ductile metallic material, which may preferably be a weldable structural steel, but may also be a ductile light metal alloy (e.g. aluminum alloy), in order to intensify the acoustic emissions behavior. The particles should be brittle at least in the temperature range of use of the component in question, e.g. at room temperature. It is advantageous if the particles are also plastically deformable in the forming temperature range, so that a certain structure (elongate or acicular) of the particles can be achieved, for example during cold work-hardening.

20 Claims, 10 Drawing Sheets

COMPONENTS MADE OF DUCTILE METALLIC MATERIAL AND METHOD FOR DETERMINING DEFORMATIONS AND/OR STRAINS BY MEANS OF SOUND EMISSION ANALYSIS

CROSS-REFERENCES TO RELATED APPLICATIONS

This application is a U.S. national application of international application Ser. No. PCT/DE98/00162 filed Jan. 19, 1998, which claims priority to German Ser. No. 197 01 776.2 filed Jan. 20, 1997.

The invention relates to components made from ductile metallic materials, for which the deformation or the load acting on them is to be determined by means of acoustic emissions analysis. On the one hand, the components can be monitored during operation, so that it is possible to detect very quickly and reliably if permissible stresses in the elastic range have been reached and/or exceeded and if excess loads have caused damage. Another possibility consists in using the components in the development phase and, for example, determining the deformation performance under the various possible loads which actually occur and taking this into account for the final structure. Of course, if the deformation performance is known, it is also possible, in addition, to determine the particular load which is active. In particular, the invention can be used for expensive components which are subject to high loads, for example in the automotive engineering sector, in aeronautics or in the construction of heavy machinery, as well as for components which, if damaged, would result in considerable potential danger.

It is known, as an inexpensive and nondestructive testing method, to use acoustic emissions analysis for various components. The monitoring can be carried out immanently and in integral form on the component. During the acoustic emissions analysis, submicroscopic local deformation is recorded, which accompany damage to the material when load is applied. The noise emissions which result from deformation when load is applied are measuring using sensitive piezoelectric sensors which are preferably coupled to the surface of the component which is to be tested. This coupling may be permanent or detachable.

Particularly in the case of highly loaded components on which high safety requirements are imposed, it is preferable to use ductile metallic materials, e.g. ductile steels. Since ductile metallic materials have only a slight acoustic emissions activity, acoustic emissions analysis can only be used to a limited extent, if at all, since the signals which can be evaluated and, in particular, the amplitudes which can be measured lie in a range which is not accessible for evaluation, and at least the necessary measurement accuracy is not sufficiently high.

Therefore, the object of the invention is to modify ductile metallic materials, and to propose a method, in such a way that components made from such materials are accessible to acoustic emissions analysis with sufficient accuracy.

According to the invention, this object is achieved, in the case of components, by means of the features of patent claim 1 and, for the method, by means of the features of claim 16. Advantageous embodiments and refinements of the invention result from using the features given in the subordinate claims.

A particulate substance which is brittle at least in the temperature range below 400° C. is added to the ductile metallic material, which may preferably be a weldable structural steel but may also be a ductile light metal alloy (e.g. aluminum alloy), in order to intensify the acoustic emissions performance. The particles should be brittle at least in the temperature range of use of the particular component, e.g. at room temperature.

It is advantageous if the particles are also plastically deformable in the forming temperature range, so that a certain structure (elongate or acicular) of the particles can be achieved, for example during cold work-hardening.

For certain materials or components, it may be advantageous to arrange or form the elongate, acicular particles orthogonally in relation to the direction of stress. In such cases, approximately spherical particles may also be contained in the component.

It has now been found that such components can advantageously be produced using a powder metallurgy process (sintering, hot isostatic pressing, inter alia), making it possible to achieve a relatively homogenous distribution of the brittle particles.

However, the particles may also be introduced into the metallic material from the surface, by being rolled in, pressed in or plated on. In this case, it is possible to achieve a locally differentiated arrangement of the brittle particles in the component, which may be advantageous for certain applications. For example, critical areas of the component can become more active in terms of acoustic emissions than uncritical areas. The latter processes result in an accumulation of the particles in the surface area of the components, and particularly stresses which exert their maximum effect in this area can be detected with greater success. The particles can be introduced at the same time as a process step which is in any case required for production of the component (shaping).

The level of brittle particles in the metal can be kept relatively low, and this low quantity has no or little adverse effect on the properties which are actually desired for the base material of the component. The levels required are less than 20% by volume, but even levels of less than 2% by volume and levels of less than 1% by volume may considerably intensify the acoustic emissions activity, which now makes even ductile materials accessible for acoustic emissions analysis.

The size of the particles should be kept within a range between 1 and 200 $\mu$m, preferably between 1 and 100 $\mu$m.

In addition to MnS, $SiO_2$, quartz glass, industrial glass materials or soldering glass, borides, nitrides or nonoxidic ceramic materials have also proven suitable materials for the particles which are to be added according to the invention, various glass materials with a certain lead content having proven more suitable than pure $SiO_2$. Soldering glass materials which, in addition to lead, also contain boron and other elements are also suitable.

When making the selection of material, the appropriate melting point should be taken into account. If the melting point is low, correspondingly lower forming temperatures for the material are possible. However, it should also be noted that the temperature range of use for the components is correspondingly reduced.

The elongate form of the particles, which has already been described as being advantageous, and can be recognized as being in acicular form in a microsection, can be achieved by means of plastic deformation resulting from mechanical or thermomechanical treatment. In conjunction with a powder metallurgy production process, the mechanical properties (e.g. strength and fracture toughness) can be varied within wide ranges.

For the various component shapes and metallic base materials, the acoustic emissions activity can be optimized by suitably selecting the number, type, size and, if appropriate, arrangement of the brittle particles. One possible criterion for optimization may be the acoustic emissions performance at the yield point of the ductile metallic material. The targeted adjustment of the acoustic emissions activity can be optimized taking into account the increased acoustic emissions at the yield point or only for the entire deformation range up to the fracture limit.

Since, in acoustic emissions analysis, the decohesion at the interfaces of particles and ductile metallic matrix material can also be utilized, it is advantageous to use particles of a material which has a lower coefficient of thermal expansion than that of the matrix material. As a result, a certain prestressing force from the matrix material acts on the particles after cooling, but this force should not lead to premature fracture of the particles.

The components according to the invention are particularly suitable for designing for certain application areas in order to be able to take into account certain loads which act on the component in question even during design. In this case, weak points can be determined and structurally compensated for.

A further option which is available when using the components according to the invention is to determine the various loads which are actually active. It is possible to detect flexural stresses, tensile stresses, torsional stresses and compressive stresses by means of acoustic emissions analysis.

It is also possible to monitor the loads which act on the component during operation, and the resultant deformation, in order, in the event of predetermined limit values being reached or exceeded, to generate a signal and to initiate replacement of a component which has suffered critical initial damage.

The measurement is in this case carried out by coupling sensitive piezo-sensors to the component, the measurement signals from which can be evaluated after sufficient amplification. In this case, one sensor, but advantageously a plurality of sensors which are locally separated, may be coupled to the component. Time-delayed or parallel evaluation of the acoustic emissions signals can be carried out selectively for each sensor. The use of a plurality of sensors may, during evaluation of the respective time delay of the measured signals, make it possible to locally assign the measurement signals to the component.

The use of the components according to the invention has surprisingly made it possible, using a simple measurement technique, to apply acoustic emissions analysis even to ductile metals with sufficient accuracy. It is possible to use a simplified electronic measurement and evaluation unit which is close to the sensor and to optimize the acoustic emissions activity.

Such components according to the invention may advantageously be designed in such a way that their contour predetermines locally limited weak points (e.g. notches, reductions in cross section) which, depending on use, provide a signal which indicates that the resistance to fracture or yield strength of the component has not yet been reached, or, in the design phase, are to test corresponding influences during the shaping and selection of materials.

When determining deformations and/or loads which act on a component which is made from a ductile metallic material and contains brittle particles in accordance with claim 1, an acoustic emissions analysis is carried out and, in the process, the number of measured burst signals is determined, and this number is then recorded and evaluated as a function of time, stress and/or elongation, so that it is possible to monitor, for example, whether predeterminable forces or moments which act on such a component are being exceeded even during use. If such a phenomenon is observed, a suitable alarm signal can be generated if necessary, so that the need to replace the corresponding component can be recognized. Generally, therefore, for reasons of simplicity, preference is given to time-dependent determination of the number of measured burst signals (occurrence rate, ring counts rate), since this can be carried out relatively easily by electronic means.

The measurement accuracy of such acoustic emissions analysis can be improved further if only the number of burst signals which lie above a predeterminable limit value are determined and taken into account. Such a limit value (threshold), in the case of measurements which use sensitive piezoelectric sensors, in particular under actual conditions of use, can be increased by means of the invention, so that not only is the acoustic emissions analysis carried out under laboratory conditions, but also the influence of disturbance variables can be reduced with the higher limit value.

The need to exchange a component according to the invention can also be established and indicated by comparing the determined number of amplitudes with at least one material- and/or component-specific, predeterminable maximum value, so that a suitable signal is generated in the event of this maximum value being exceeded.

The invention is to be described in more detail below with reference to exemplary embodiments. In the drawing.

Figure 1:
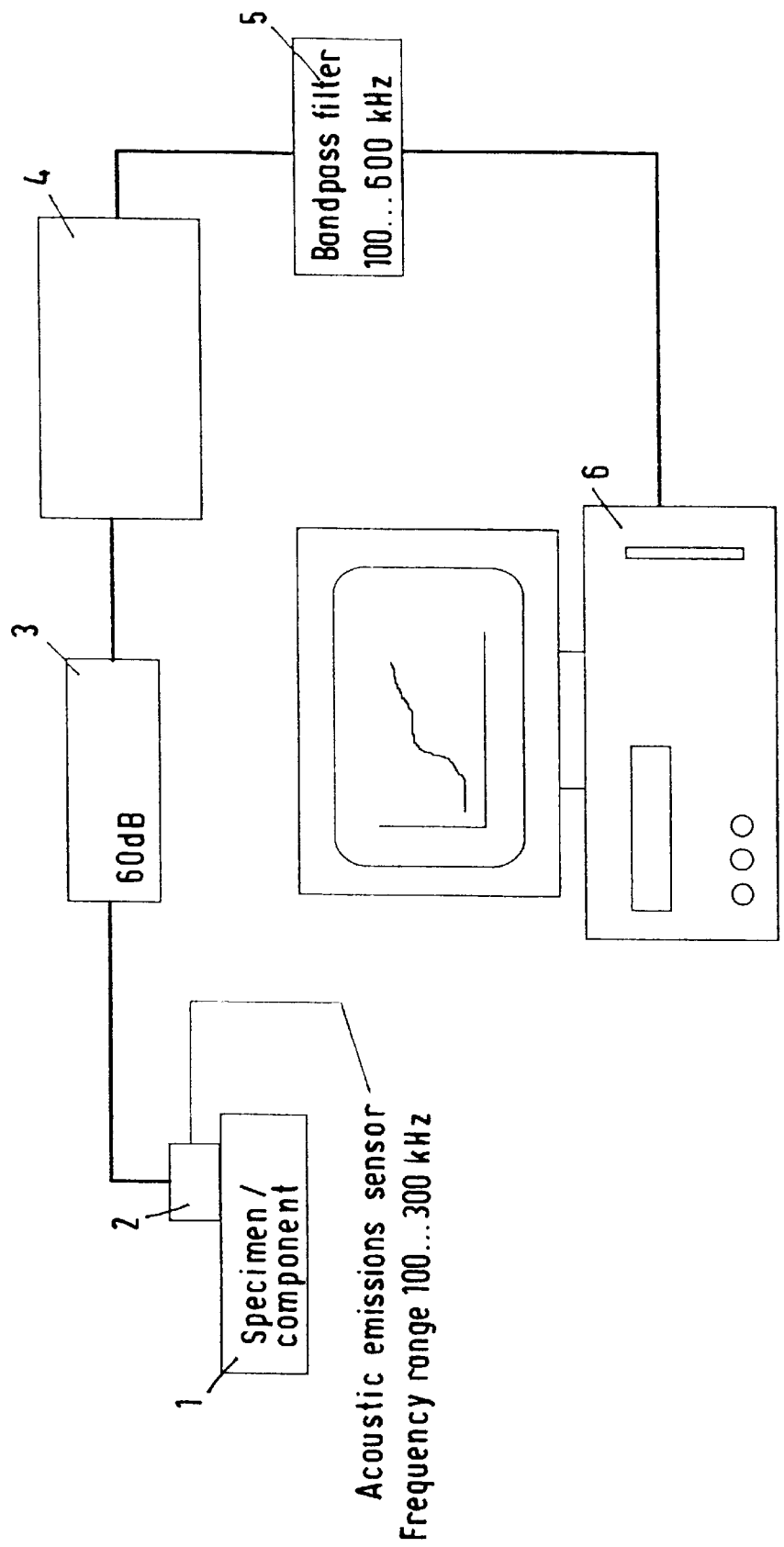
FIG. 1 shows a block circuit diagram of a measurement arrangement for acoustic emissions analysis.

FIG. 1 shows a block circuit diagram of a measurement arrangement for carrying out an acoustic emissions analysis. An acoustic emissions sensor 2 is attached and acoustically coupled to the component 1. The acoustic emissions sensor 2 may be permanently or detachably connected to the component 1.

Via a preamplifier 3, a coupler 4 and a bandpass filter 5, the amplified and selected acoustic emissions signals are passed to an evaluation unit 6 (e.g. personal computer). The evaluation is carried out using calibration values or curves which are stored in a memory of the evaluation unit 6 and are compared with the measured values in order, for example, to record the deformation or the yield point or if the latter has been exceeded.

Figure 2:
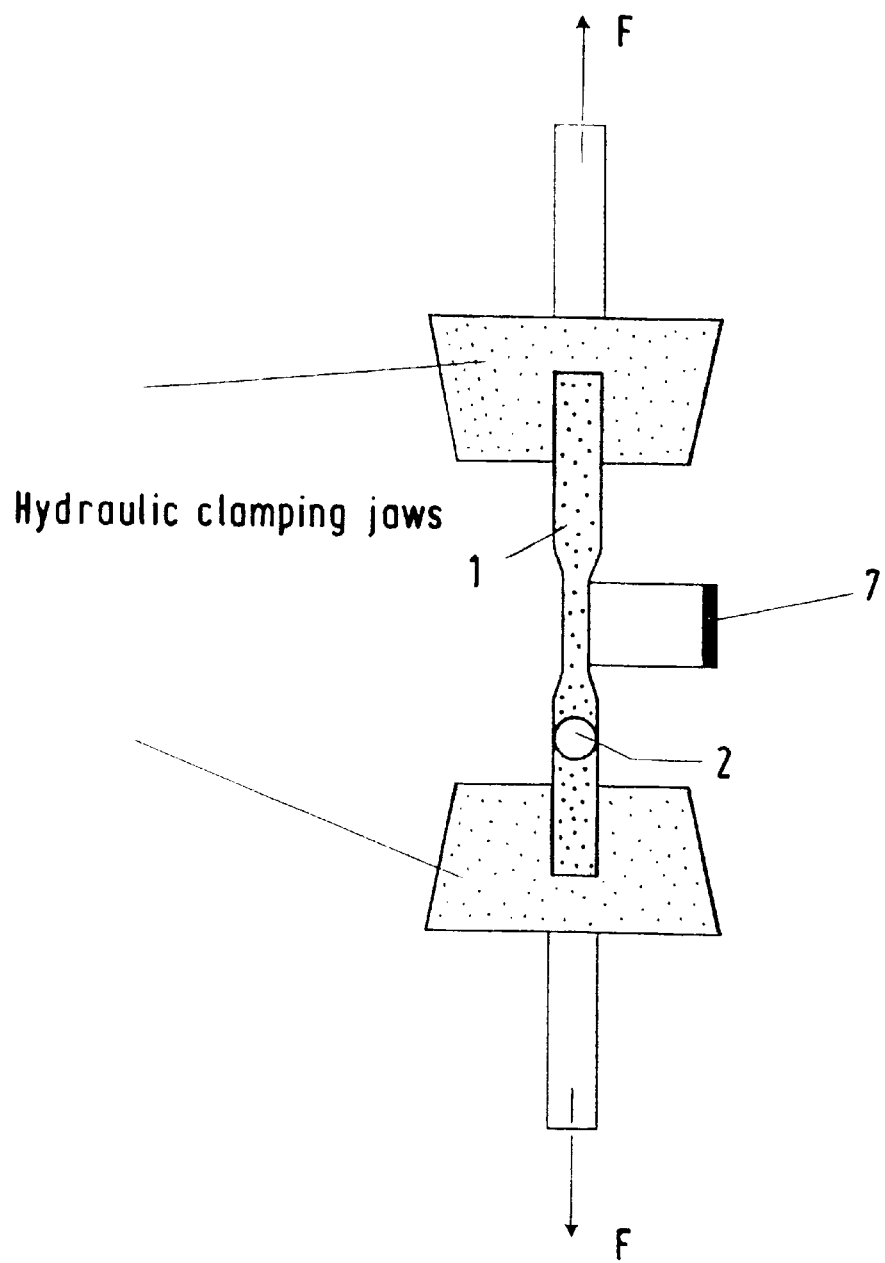
FIG. 2 shows a diagrammatic illustration of a component undergoing a tensile test.

FIG. 2 diagrammatically illustrates the arrangement of a tensile test carried out on a tensile bar as component 1. In this test, a defined tensile force or a correspondingly predeterminable force profile is applied, and the elongation (deformation) of the component is measured in parallel using a conventional elongation sensor 7 (e.g. by means of DMS) and an acoustic emissions sensor 2.

Figure 3:
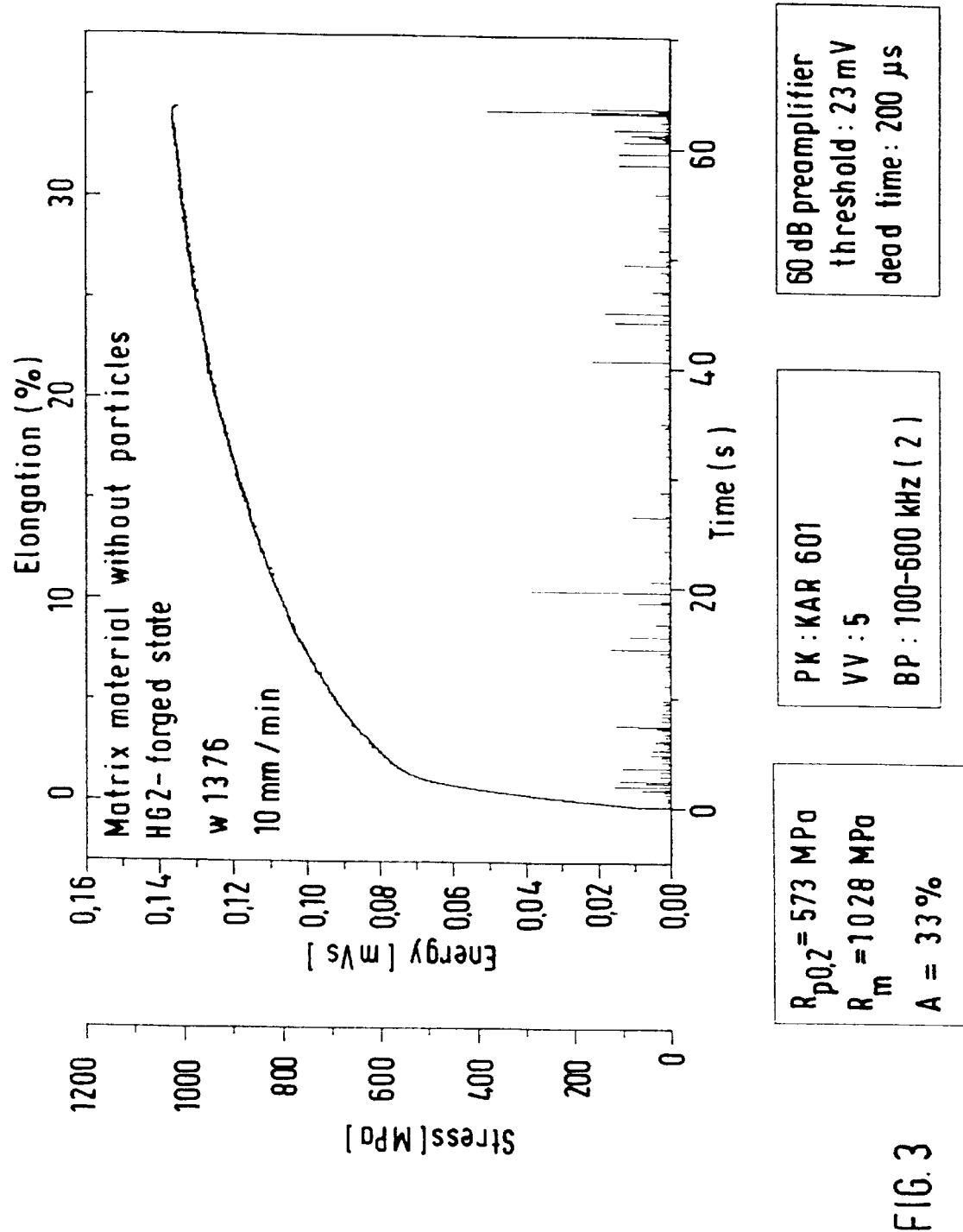
FIG. 3 shows a diagram of the stress measured using acoustic emissions analysis for a conventional component.

The diagram shown in FIG. 3 gives measured value curves measured in accordance with FIG. 2 for a conventional component made from a ductile steel containing 8.8% by mass Cr, 8.4% by mass Ni, 4.2% by mass Mo, 1.8% by mass Mn, 1.7% by mass Si, 0.5% by mass C and 0.02% by mass S. The tensile stress curve is shown as a function of time (abscissa bottom) and as a function of the elongation (abscissa top). In addition, the diagram includes the curve of the acoustic emissions energy measured.

The individual acoustic emissions energy amplitudes shown that these signals do not make it possible to evaluate the deformation (elongation) or to detect if the yield point of this material has been exceeded, since it is not possible to detect and demonstrate a relationship between these measured values and the stress on the component.

Figure 4:
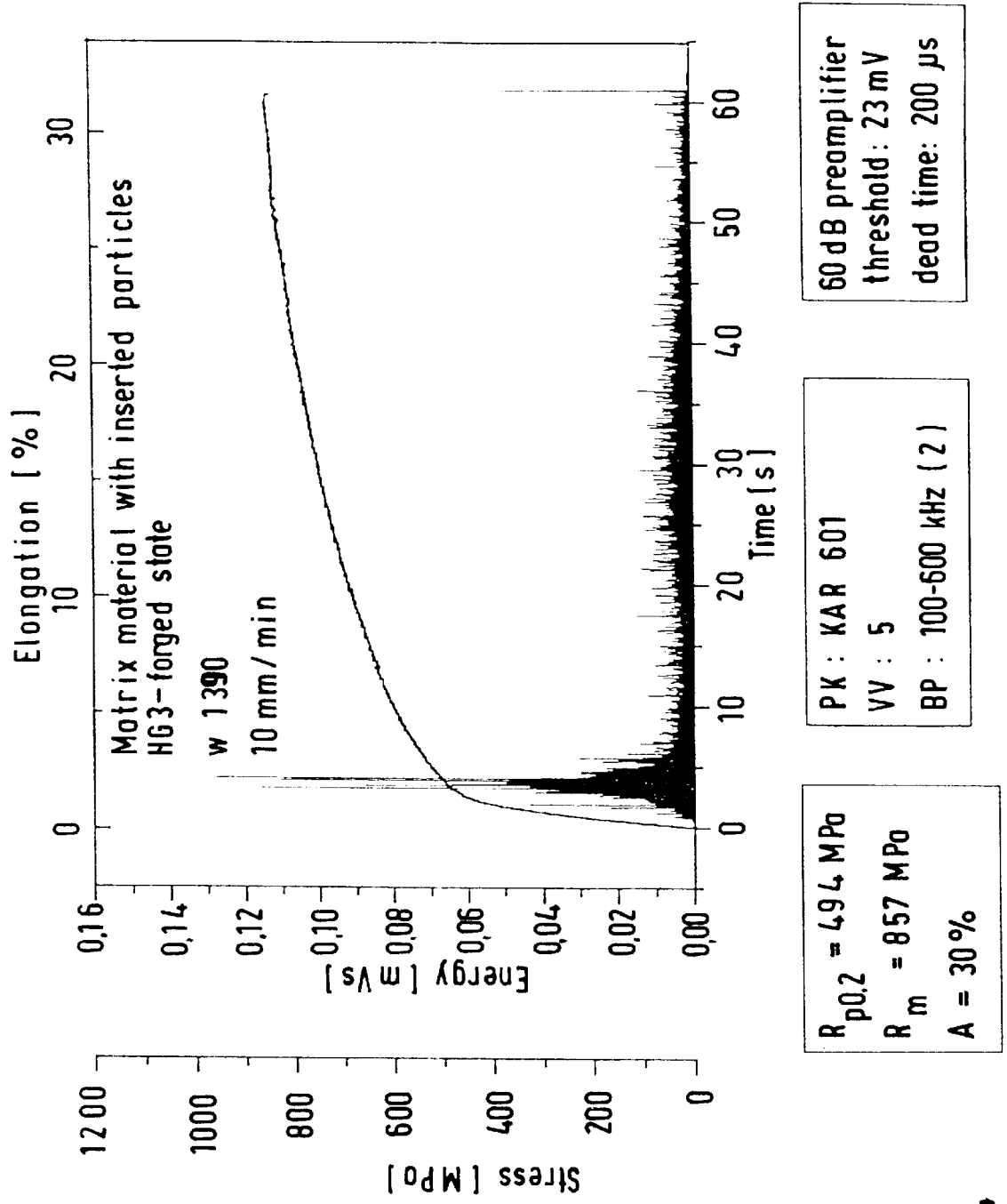
FIG. 4 shows a diagram of the stress measuring using acoustic emissions analysis for a component according to the invention.

In contrast, it can clearly be seen from the diagram shown in FIG. 4 that both the distribution and the amplitudes of the values measured using the acoustic emissions sensor have much more meaning. This is the case for both the magnitude and the distribution of the individual amplitudes. The measured values reach a level which lies above the noise error, and consequently unambiguous classification is possible. The diagram also clearly shows the unambiguous recording of the yield point.

Figure 5:
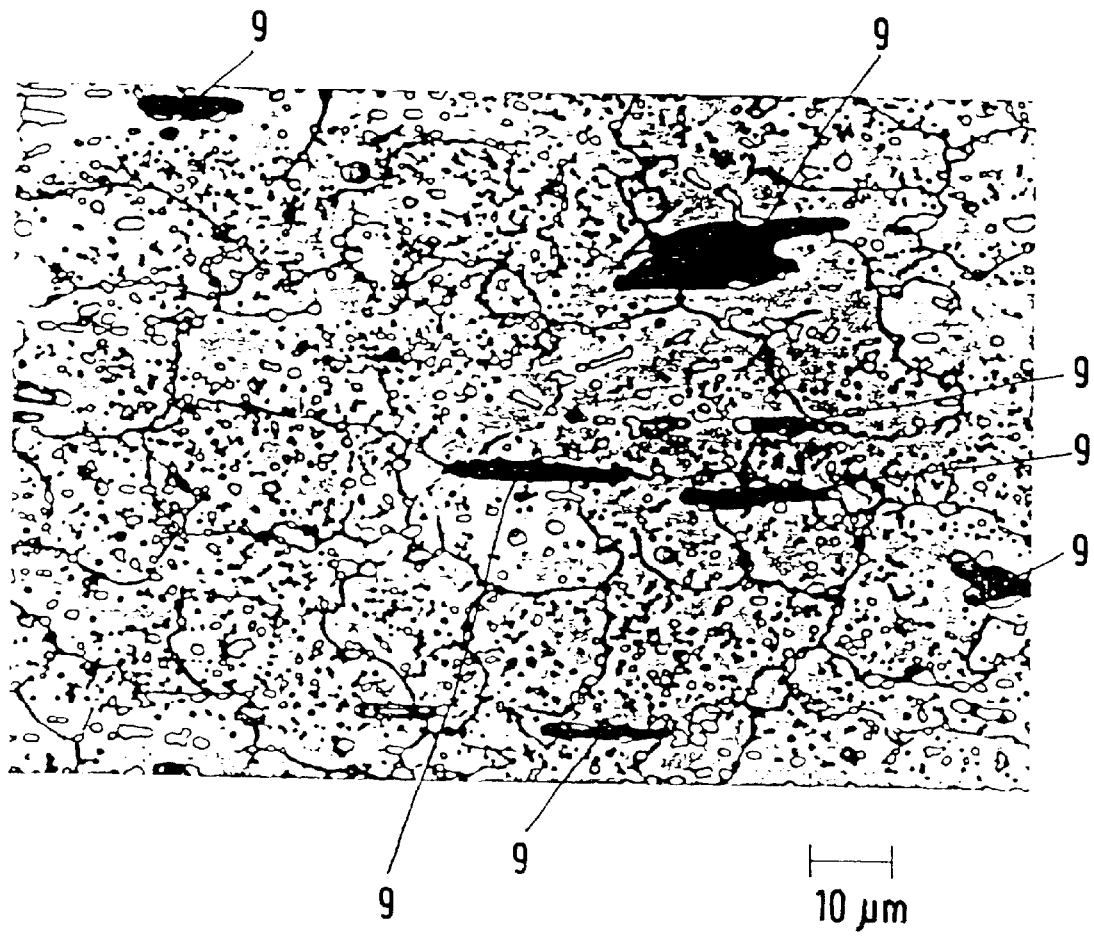
FIG. 5 shows an enlarged microsection of a material for a component according to the invention with brittle particles incorporated in the base material.

In this example, a component according to the invention was used, made from a steel containing 8.8% by mass Cr, 8.4% by mass Ni, 4.2% by mass Mo, 1.8% by mass Mn, 1.7% by mass Si, 0.5% by mass C, 0.02% by mass S and with a homogeneous incorporation by powder metallurgy means of 0.5% by mass MnS particles 9. The MnS particles were subject to plastic deformation by hot deformation, as can be seen in FIG. 5. In this example, the size of the deformed particles 9 lies only in the area of 10 $\mu$m.

The MnS particles 9 are brittle at room temperature and, during deformation, this has the surprising result that it is possible to detect whether the yield point has been exceeded and any plastic deformation beyond this limit even for materials which were not originally accessible to acoustic emissions analysis.

Figure 6:
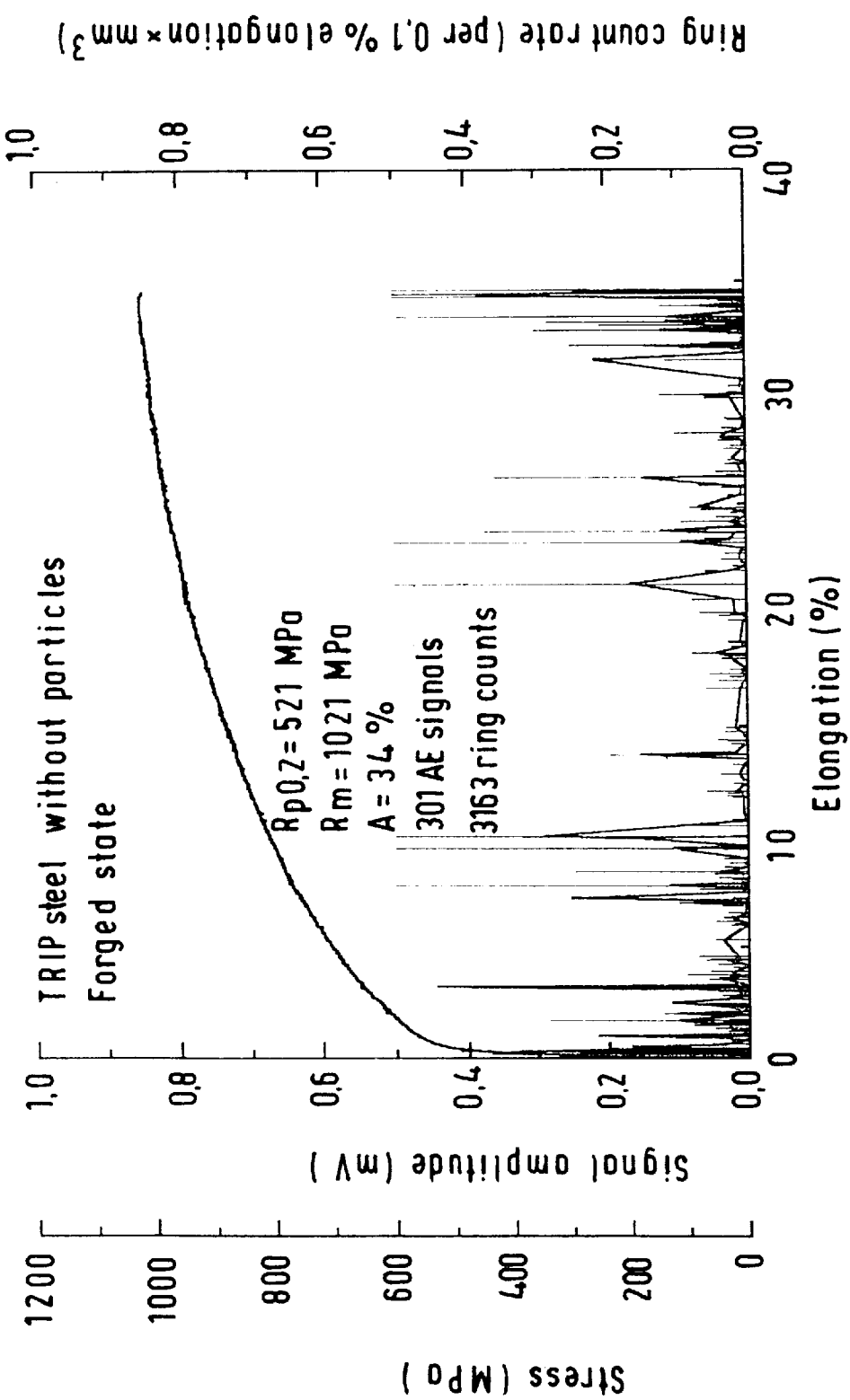
FIG. 6 shows a diagram of a component in accordance with FIG. 3 with further reference parameters.
Figure 7:
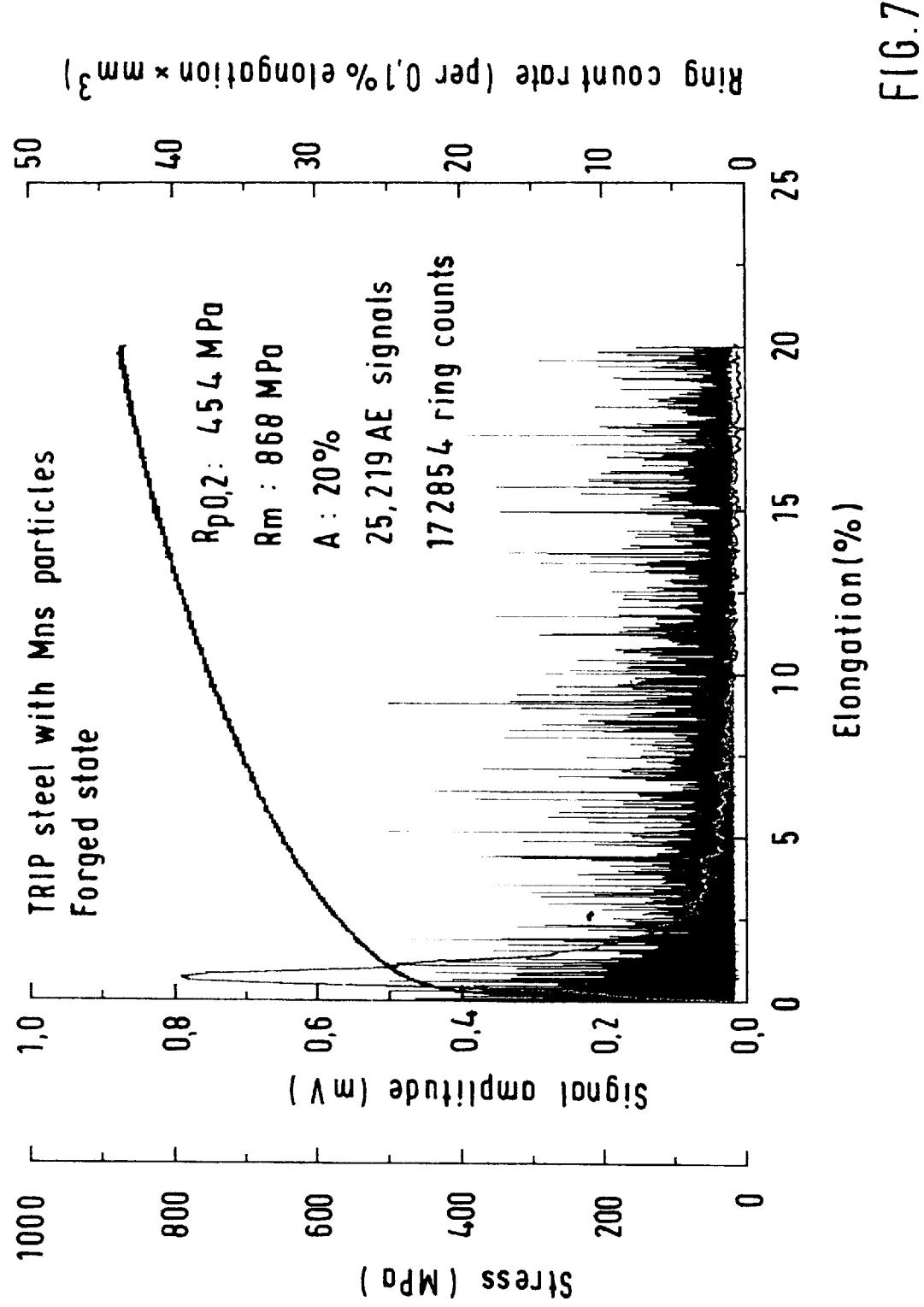
FIG. 7 shows a diagram of a component in accordance with FIG. 4 with further reference parameters.

FIGS. 6 and 7 show further diagrams in which acoustic emissions analysis has been carried out on components, with further reference parameters, the corresponding components made from a material having a composition which corresponds to that in accordance with FIG. 3 being used for the diagram in FIG. 6 and a composition which corresponds to that in accordance with FIG. 4 for the diagram in FIG. 7.

Figure 8:
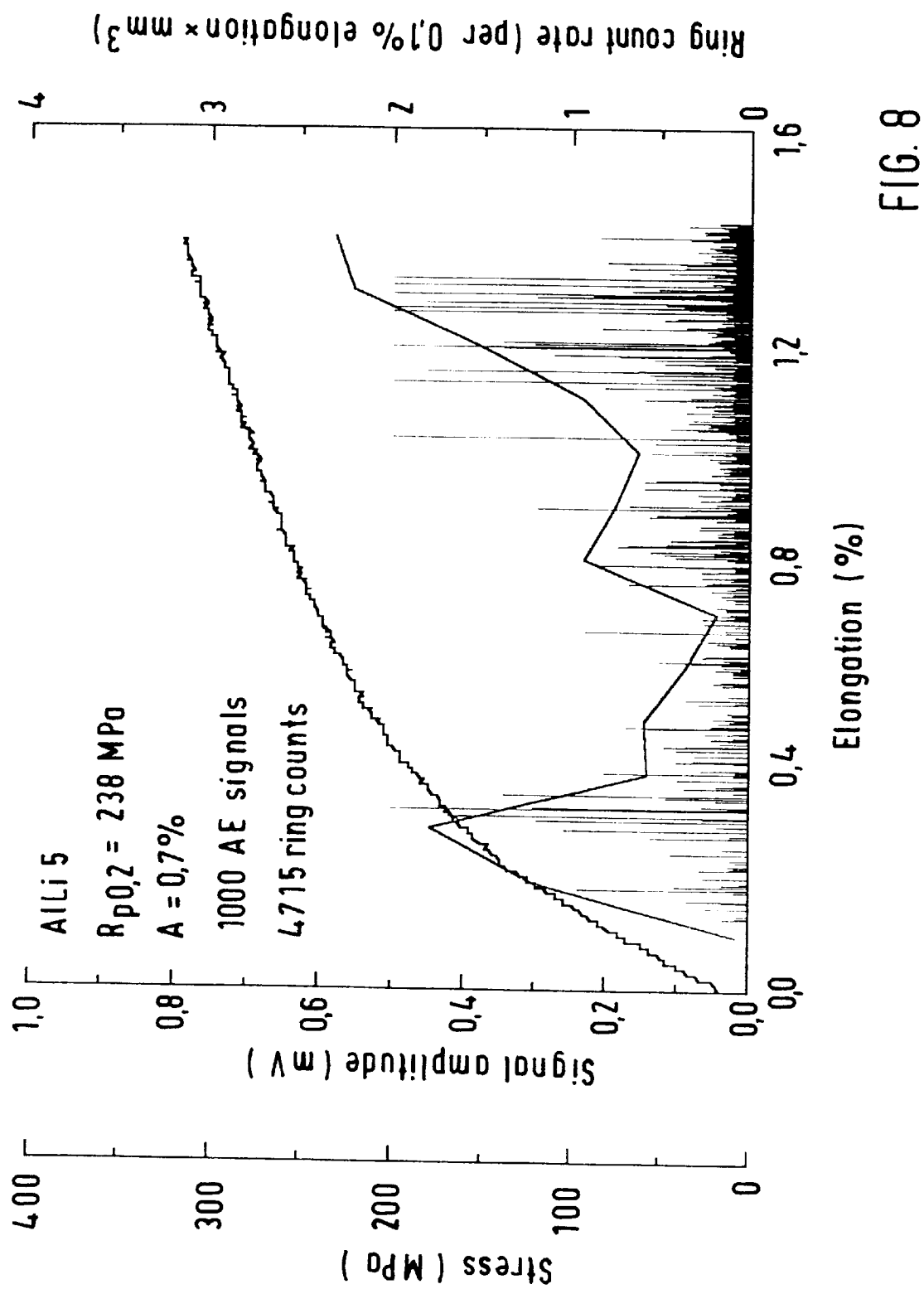
FIG. 8 shows a diagram for the entire stress using acoustic emissions analysis on a conventional component made from AlLi 5.
Figure 9:
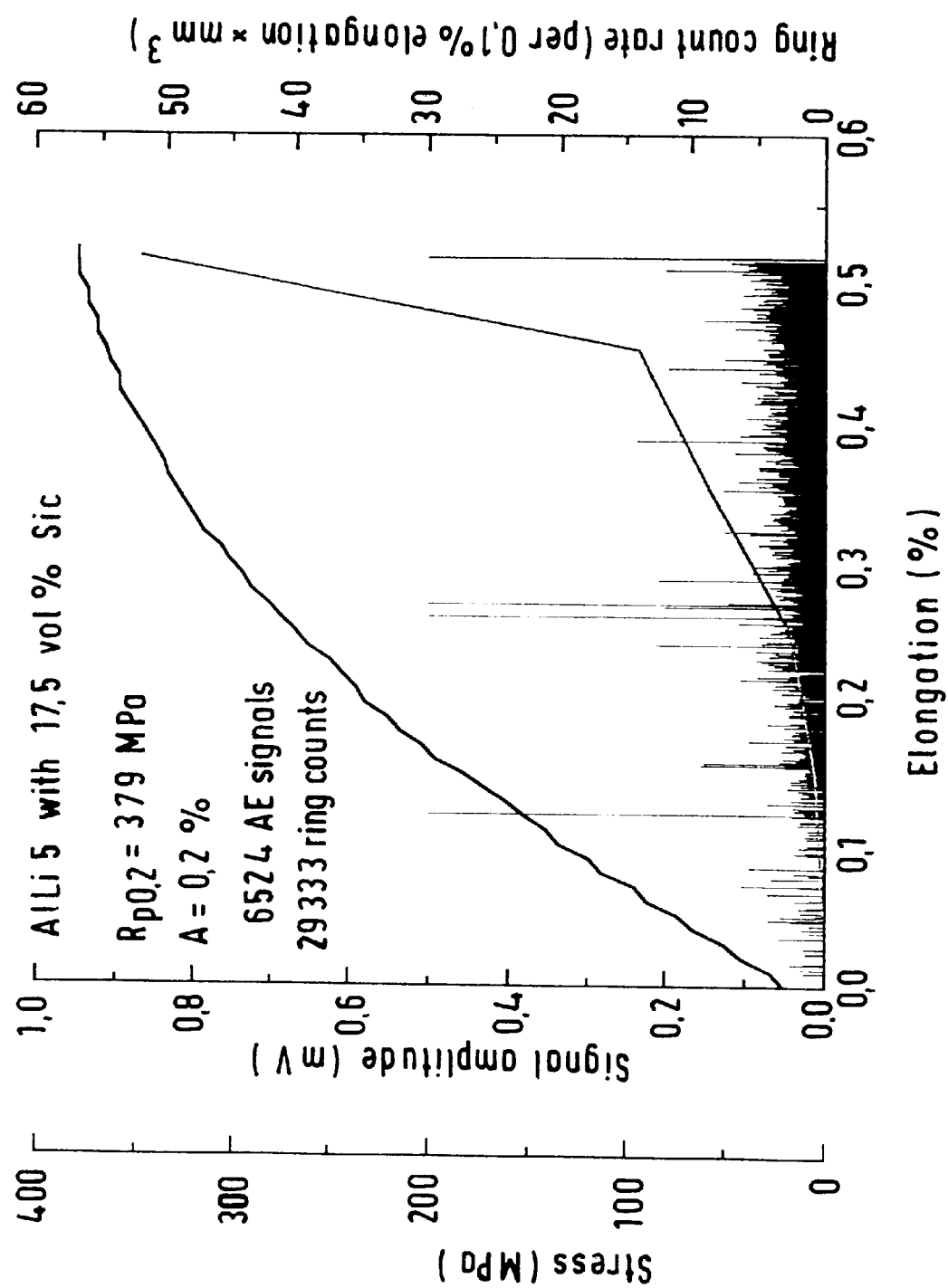
FIG. 9 shows a diagram of the stress measured on a component which has been modified according to the invention and is made from AlLi 5 containing SiC.

FIGS. 8 and 9 show diagrams for components made from AlLi 5, FIG. 8 showing the corresponding measured values for acoustic emissions analysis carried out on a conventional AlLi 5, and FIG. 9 showing the measured values for an AlLi 5 which has been modified according to the invention and to which brittle particles of SiC (17.5% by volume) have been added.

Figure 10:
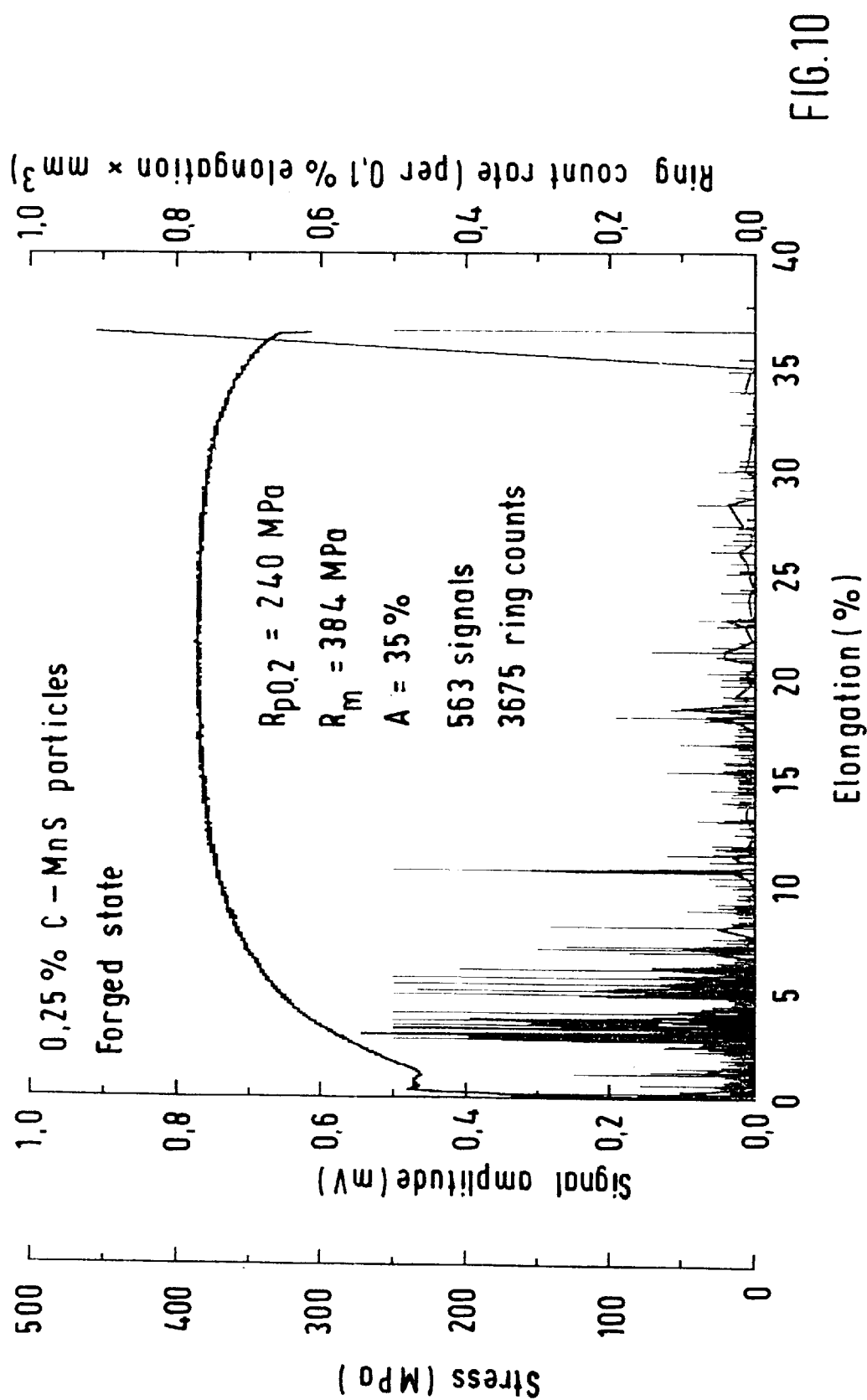
FIG. 10 shows a diagram of the stress measured on a component according to the invention made from a 0.25% C steel containing MnS particles.

FIG. 10 then also shows a diagram of stresses measured using an acoustic emissions analysis carried out on a component according to the invention made from a 0.25% C steel containing MnS particles (1% by volume).

What is claimed is:

1. A component made from ductile, metallic material adapted for determining at least one of deformation and loads which act on this component by means of acoustic emissions analysis, comprising: a component made from ductile, metallic material, and particles which are brittle at least at a temperature of below 400° C. and have a mean particle size of between 1 and 200 $\mu$m have been added to the ductile metallic material to allow for acoustic emissions analysis.

2. The component as claimed in claim 1, wherein the brittle particles are plasticaliy deformable at below their melting temperature.

3. The component as claimed in claim 1, wherein the brittle particles are introduced by at least one of rolling in pressing in and plating on.

4. The component as claimed in claim 1, wherein the brittle particles are added to the material in an amount of <20% by volume.

5. (Retyped without change) The component as claimed in claim 4, wherein the brittle particles are added to the material in an amount of <2% by volume.

6. The component as claimed in claim 1, wherein the brittle particles comprise brittle particles of at least one of MnS and $SiO_2$ (quartz glass).

7. The component as claimed in claim 1, wherein the brittle particles comprise brittle particles of at least one of borides, nitrides and nonoxidic ceramic materials.

8. The component as claimed in claim 1, wherein the particles in the component are introduced in a locally differentiated manner.

9. The component as claimed in claim 1, wherein the brittle particles are deformed in a plastic, elongated manner by means of a mechanical or thermomechanical treatment.

10. The component as claimed in claim 1, wherein at least one of the nature, number and size of the brittle particles in the material is set in such a way that a high acoustic emission activity can be achieved at the yield strength of the material.

11. The component as claimed in claim 1, wherein at least one of the type, number and size of the brittle particles in the material is set in such a way that the material remains active in terms of acoustic emissions throughout the entire deformation process.

12. The component as claimed in claim 1, wherein the contour is designed so as to form locally limited, predeterminable weak points.

13. A method for producing the component as claimed in claim 1, wherein the component is produced by powder metallurgy.

14. A method for producing the component as claimed in claim 1, wherein the component is produced by melt metallurgy.

15. A method for determining deformation or loads on a component made from a ductile metallic material comprising:

providing a component made from ductile metallic material into which particles which are brittle at a temperature of below 400° C. have been added, and measuring the number of burst signals obtained from said ductile metallic material as a function of at least one of time, stress and elongation, by means of acoustic emissions analysis.

16. The method as claimed in claim 15, wherein the number of burst signals above a predeterminable limit value is determined.

17. The method as claimed in claim 15, wherein a certain number of burst signals is compared with at least one of material-specific predeterminable maximum values and component-specific predeterminable maximum values, and a signal is generated if these values are reached or exceeded.

18. The component as claimed in claim 2 wherein the brittle particles are introduced by at least one of rolling in, pressing in and plating on.

19. The component as claimed in claim 2 wherein the brittle particles are added to the material in an amount of <20% by volume.

20. The component as claimed in claim 19 wherein the brittle particles are added to the material in an amount of <2% by volume.

* * * * *